United States Patent [19]

Ohtawa

[11] Patent Number: 5,266,583
[45] Date of Patent: Nov. 30, 1993

[54] ANGITOTENSIN II ANTAGONIST

[75] Inventor: Masakatsu Ohtawa, Tokyo, Japan

[73] Assignee: Merck & Co., Inc., Rahway, N.J.

[21] Appl. No.: 940,253

[22] Filed: Sep. 1, 1992

[51] Int. Cl.⁵ .................... C07D 403/10; A61K 31/41
[52] U.S. Cl. ..................................... 514/381; 548/253
[58] Field of Search ......................... 514/381; 548/253

[56] References Cited

FOREIGN PATENT DOCUMENTS 0459136 12/1991 European Pat. Off. ............ 548/253

Primary Examiner—David B. Springer
Attorney, Agent, or Firm—Robert J. North; William H. Nicholson; Joseph F. DiPrima

[57] ABSTRACT

A human urinary metabolite of Losartan has been isolated and identified as structure I.

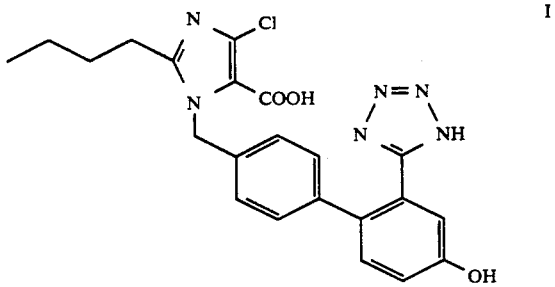

This compound is an active angiotensin II receptor antagonist useful in the treatment of hypertension and congestive heart failure.

3 Claims, No Drawings

ANGITOTENSIN II ANTAGONIST

BACKGROUND OF THE INVENTION

Losartan is a well known angiotensin-II receptor antagonist of structural formula II. It is also known to be metabolized to the compound of Structure III.

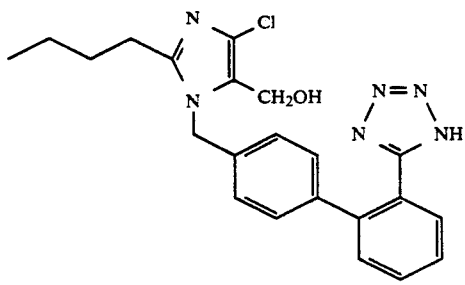

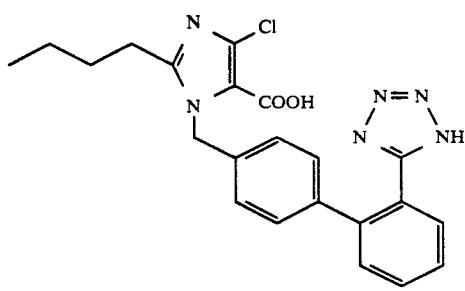

Now with the present invention there is provided another metabolite of Losartan of Structure I which is an active angiotensin II receptor antagonist.

DETAILED DESCRIPTION OF THE INVENTION

The novel compound of this invention has Structural formula I:

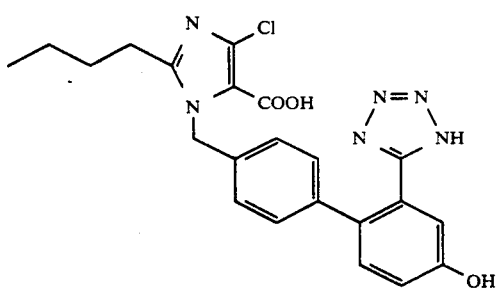

or a pharmaceutically acceptable salt thereof.

The novel compound of this invention was first isolated from 500 ml urine sample collected after single oral administration of 200 mg/man of Losartan (II) to humans. The methods for the separation of the compound comprised three steps.

The first step was rough separation of the compound by extracting with two sample-volume of t-butyl methyl ether (TBME) twice under acidic conditions and subjecting the extract to preparative HPLC. The chromatographic conditions were as follows:
Guard Column: Senshu Pak ODS-1031-N 4.6 mm×30 mm
Separation Column: Senshu Pak ODS-4251-N 10 mm×250 mm
Column Temp.: 40° C.
Mobile Phase:
  A; $CH_3CN$, B: 25 mM phosphate buffer (pH 2.8)
  A:B=51:49→72:28 gradient for 40 min.
Flow Rate: 2.0 ml/min.
Detector: 310 nm
Retention Time: 9-11 min.

The fraction corresponding to the peaks (retention time 9-11 min) on HPLC were collected.

The second step was further separation of the compound obtained from the rough fraction by extraction with TBME and reseparation by the preparative HPLC with the following conditions:
Guard Column: Senshu Pak ODS-1031-N 4.6 mm×30 mm
Separation Column: Senshu Pak ODS-4251-N 10 mm×250 mm
Column Temp.: 40° C.
Mobile Phase:
  A; $CH_3CN$, B: 25 mM phosphate buffer (ph 2.8)
  A:B=30:70 for 7.5 min.; 30:70→40:60 gradient for 7.5 min.; 40:60 for 20 min.
Flow Rate:
  1.8 ml/min for 7.5 min.
  2.0 ml/min to finish
Detector: 230 nm
Retention Time: about 29 min.

The last step was the purification by TLC. The peak fraction having retention time at 29 min. on the HPLC was collected ans applied to TLC plate. TLC was carried out on precoated silica-gel glass plate, 0.25 mm thickness. The developing solvent was as follows: $CHCl_3$/MeOH/AcOH (30/3/1,v/v/v). After development, the compound was visualized under UV light. The appropriate area (Rf value 0.2) on the silica-gel plate was removed and eluted with methanol. The purified metabolite was analyzed by HPLC. The chromatographic conditions were as follows:
Column:
  Pre; MPLC NewGuard RP-18, 15 mm×3.2 mm I.D.
  Sep: CAPCELL PAK C18, 250 mm×4.6 mm I.D.
Column Temp.: 40° C.
Mobile Phase:
  A; $CH_3CN$, B: 25 mM phosphate buffer (pH 2.8)
  A:B=20:80→30:70 gradient for 15 min.; 30:70→45:55 gradient for 15 min.
Flow Rate: 1.0 ml/min.
Detector: 230 nm
Retention Time: about 25.8 min.

The structure of the metabolite was assigned based upon mass and spectroscopic analysis.

In the FAB mass spectrum of I, there is a protonated molecular ion at m/z 453 and a benzylic methylene proton signal at 5.65 ppm in the nmr spectrum. However, the signals corresponding to the 2-butyl sidechain protons of II were present and the aromatic ring protons which appeared at 7.42-7.55 ppm in II were shifted upfield to 6.88-7.21 ppm. The proton decoupling indicated that this metabolite is substituted at the position corresponding to either biphenyl-C4' or -C5' of II. Further the NOESY experiment showed that this metabolite is substituted at the biphenyl -C4'. From these results, the metabolite was assigned the Structure I.

The compound of this invention forms salts with various inorganic and organic acids and bases which are also within the scope of the invention. Such salts include ammonium salts, alkali metal salts such as sodium and potassium salts, alkaline earth metal salts like calcium and magnesium salts, salts with organic bases; e.g., dicyclohexylamine salts, N-methyl-D-glucamine salts, salts with amino acids like arginine, lysine, and the like. Also, salts with organic and inorganic acids may be prepared; e.g., HCl, HBr, $H_2SO_4$, $H_3PO_4$, methanesulfonic, toluensulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compound of this invention is useful in treating hypertension. It is also of value in the management of acute and chronic congestive heart failure and angina. It is also expected to be useful in primary and secondary hyperaldosteronism, renal diseases such as diabetic nephropathy, glomerulonephritis, glomerular sclerosis, nephrotic syndrome, hypertensive nephrosclerosis, end stage renal disease, renal transplant therapy, renovascular hypertension, scleroderma, left ventricular dysfunction, systolic and diastolic dysfunction diabetic retinopathy, in the management of vascular disorders such as migraine or Raynaud's disease, as prophylaxis to minimize the atherosclerotic process, in neointimal hyperplasia following angioplasty or vascular injury and to retard the onset of type II diabetes. The application of the compound of this invention for these and similar disorders will be apparent to those skilled in the art.

The compound of this invention is also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of the compound of this invention. For this use, the compound of this invention may also be used in combination with other medications for the treatment of glaucoma including choline esterase inhibitors such as physostigmine salicylate or demecarium bromide, parasympathomimetic agents such as pilocarpine nitrate, $\beta$-adrenergic antagonists such as timolol maleate, adrenergic agonists such as epinephrine and carbonic anhydrase inhibitors such as TRUSOPT TM.

In the management of hypertension and the clinical conditions noted above, the compound of this invention may be utilized in compositions such as tablets, capsules or elixirs for oral administration, suppositories for rectal administration, sterile solutions or suspensions for parenteral or intramuscular administration, and the like. The compound of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 5.0 to 500 mg. per patient per day; more preferably about 5 to 300 mg. per patient per day.

The compound of this invention can also be administered in combination with other antihypertensives and/or diuretics. For example, the compound of this invention can be given in combination with diuretics such as hydrochlorothiazide, chlorothiazide, chlorthalidone, methyclothiazide, furosemide, ethacrynic acid, triamterene, amiloride, atriopeptin and spironolactone; calcium channel blockers, such as diltiazem, felodipine, nifedipine, amlodipine, nimodipine, isradipine, nitrendipine and verapamil; $\beta$-adrenergic antagonists such as timolol, atenolol, metoprolol, propanolol, nadolol and pindolol; angiotensin converting enzyme inhibitors such as enalapril, lisinopril, captopril, ramipril, quinapril and zofenopril; renin inhibitors such as A-69729 and FK 906 and FK 744; $\alpha$-adrenergic antagonists such as prazosin, doxazosin, and terazosin; sympatholytic agents such as methyldopa, clonidine and guanabenz, atriopeptidase inhibitors (alone or with ANP) such as UK-79300; serotonin antagonists such as ketanserin; $A_2$-adenosine receptor agonists such as CGS 22492C; potassium channel agonists such as pinacidil and cromakalim; and various other antihypertensive drugs including reserpine, minoxidil, guanethidine, hydralazine hydrochloride and sodium nitroprusside as well as combinations of the above-named drugs.

Combinations useful in the management of congestive heart failure include, in addition, the compound of this invention with cardiac stimulants such as dobutamine and xamoterol and phosphodiesterase inhibitors including amrinone and milrinone.

Typically, the individual daily dosages for these combinations can range from about one-fifth of the minimally recommended clinical dosages to the maximum recommended levels for the entities when they are given singly.

To illustrate these combinations, the angiotensin II antagonist of this invention can be effectively combined at levels of the 1.0-500 milligrams per day range with the following compounds at the indicated per day dose range: hydrochlorothiazide (6-100 mg), chlorothiazide (125-500 mg), ethacrynic acid (5-200 mg), amiloride (5-20 mg), furosemide (5-80 mg), propanolol (10-480 mg), timolol maleate (1-20 mg), methyldopa (125-2000 mg), felodipine (1-20 mg), nifedipine (5-120 mg), nitrendipine (5-60 mg) and diltiazem (30-540 mg). In addition, triple drug combinations of hydrochlorothiazide (5-100 mg) plus amiloride (5-20 mg) plus the compound of this invention (1-500 mg) or hydrochlorothiazide (5-100 mg) plus timolol maleate (5-60) plus the compound of this invention (1-500 mg) or hydrochlorothiazide (5-200 mg) and nifedipine (5-60 mg) plus the compound of this invention (1-500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

FORMULATION EXAMPLES

Typical Pharmaceutical Compositions Containing the Compound of the Invention

A: Dry Filled Capsules Containing 50 mg of Active Ingredient Per Capsule

| Ingredient | Amount per Capsule (mg) |
| --- | --- |
| Compound I | 50 |
| Lactose | 149 |
| Magnesium stearate | 1 |
| Capsule (size No. 1) | 200 |

Compound I can be reduces to a No. 60 powder and the lactose and magnesium stearate can then be passed through a No. 60 blotting cloth onto the powder. The combined ingredients can then be mixed for about 10 minutes and fikkes into a No. 1 dry gelatin capsule.

B: Tablet

A typical tablet would contain Compound I (25 mg), pregelatinized starch USP (82 mg), microcrystaline cellulose (82 mg) and magnesium stearate (1 mg).

C: Suppository Formulation

A typical suppository formulations for rectal administration can contain Compound I (1-25 mg), butylated hydroxyanisole (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium clacium edetate and a hydrogenated vegetable oil (675-1400 mg) such as Suppocire L, Wecobee FS, Wecobee M, Witepsols, and the like, for the polyethylene glucol. Further, these suppository formulations can also include another active ingredient such as another antihypertensive and/or a diuretic and/or an angiotensin converting enzyme and/or a calcium channel blocker in pharmaceutically effective amounts.

D: Injection

A typical injectable formulation would contain Compound I (5.42 mg), sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertansive and/or a diuretic and/or an angiotensin converting enzyme inhibitor and/or a calcium channel blocker.

What is claimed is:

1. A compound of structural formula:

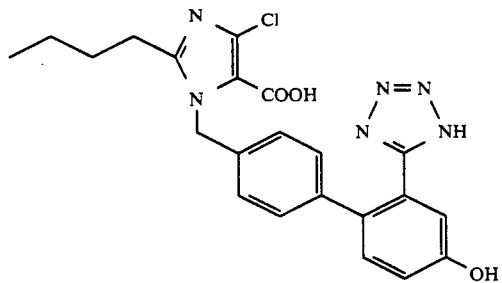

or a pharmaceutically acceptable salt thereof.

2. A pharmaceutical formulation for the treatment of hypertension comprising a pharmaceutically acceptable carrier and an effective amount of the compound of claim 1.

3. A method of treating hypertension and congestive heart failure which comprises the administration of an effective amount of the compound of claim 1 to a patient in need of such treatment.

* * * * *